United States Patent [19]

Nelson et al.

[11] Patent Number: 4,789,544

[45] Date of Patent: Dec. 6, 1988

[54] CO-VACCINATION USING NON-O-CARBOHYDRATE SIDE-CHAIN GRAM-NEGATIVE BACTERIA PREPARATION

[75] Inventors: Ralph Nelson, Shawnee, Kans.; Gerald Schlink, Irwin, Mo.

[73] Assignee: Midcon Labs. Inc., Lamar, Mo.

[21] Appl. No.: 127,492

[22] Filed: Dec. 1, 1987

Related U.S. Application Data

[63] Continuation-in-part of Ser. No. 866,451, May 23, 1986, abandoned.

[51] Int. Cl.$^4$ .................... A61K 39/02; A61K 39/10; A61K 39/108; A61K 39/104
[52] U.S. Cl. ........................................ 424/92; 424/87; 424/93
[58] Field of Search ............................. 424/87, 92, 93

[56] References Cited

U.S. PATENT DOCUMENTS

| | | | |
|---|---|---|---|
| 3,148,120 | 9/1964 | Westphal | 424/92 |
| 3,185,624 | 5/1965 | Nakazawa | 424/92 |
| 3,401,219 | 9/1968 | Zeissig | 424/92 X |
| 3,438,862 | 4/1969 | Work | 424/92 X |
| 4,016,253 | 4/1977 | Switzer et al. | 424/92 |
| 4,167,560 | 9/1979 | Wohler, Jr. | 424/92 |
| 4,428,931 | 1/1984 | Tolman et al. | 424/87 |
| 4,455,142 | 6/1984 | Martins et al. | 424/19 |
| 4,469,672 | 9/1984 | Harris | 424/92 X |
| 4,626,430 | 12/1986 | Kucera | 424/92 |
| 4,663,160 | 5/1987 | Tsay et al. | 424/87 |
| 4,687,738 | 8/1987 | Ginnaga et al. | 424/92 X |

FOREIGN PATENT DOCUMENTS

| | | |
|---|---|---|
| 0089283 | 3/1983 | European Pat. Off. . |
| 0158282 | 4/1985 | European Pat. Off. . |
| 80/00021 | 4/1980 | PCT Int'l Appl. . |
| 012222 | 5/1987 | PCT Int'l Appl. . |
| 1085956 | 9/1964 | United Kingdom . |
| 2076287A | 8/1981 | United Kingdom . |

OTHER PUBLICATIONS

M. I. Marks, et al., Biological Abstracts, No. 39459, vol. 74, 1982.
J. D. Baumgartner, et al., Prevention of Gram-Negative Shock and Death in Surgical Patients by Antibody to Endotoxin Core Glycolipid, The Lancet, pp. 59-63, Jul. 13, 1985.
L. M. Mutharia, et al., Monoclonal Antibodies Specific for *Escherichia coli* J5 Lipopolysaccharide: Cross-Reaction with Other Gram-Negative Bacterial Species, Infection and Immunity, Sep. 1984, pp. 631-636, vol. 45, No. 3.
M. J. Nelles, et al., Mouse Monoclonal Antibodies Reactive with J5 Lipopolysaccharide Exhibit Extensive Serological Cross-Reactivity with a Variety of Gram-Negative Bacteria, Infection and Immunity, Dec. 1984, pp. 677-681, vol. 46, No. 3.
B. W. Fenwick, et al., Biological Abstracts, vol. 82, 1986, No. 82938.
D. Martinez, et al., Prophylaxis of *Pseudomonas aeruginosa* Infections in Leukopenic Mice by a Combination of Active and Passive Immunization, Eur. J. Clin. Microbiology, Apr. 1985, pp. 186-189, vol. 4, No. 2.
A. I. Braude, et al., Immunization Against Nosocomial Infection, The Amer. J. of Med., vol. 70, pp. 463-466, Feb. 1981.
D. L. Dunn, et al., Immunotherapy of Gram-Negative Bacterial Sepsis: Enhanced Survival in a Guinea Pig Model by use of rabbit Antiserum to *Escherichia coli* J5, Surgery, vol. 92, No. 2, pp. 212-219.
C. Galanos, et al., Preparation and Properties of Antisera against the Lipid-A Component of Bacterial Lipopolysaccharides, Eur. J. Biochem, vol. 24, pp. 116-122, 1971.
L. B. Corbeil, et al., Immunity to Pasteurellosis in Compromised Rabbits, Am. J. Vet. Res., vol. 44, No. 5, pp. 845-850.
A. I. Braude, et al., Antibody to Cell Wall Glycolipid of Gram-Negative Bacteria: Induction of Immunity to Bacteremia and Endotoxemia, The Jour. Inf. Dis., vol. 156, Supplement, Aug. 1977.
M. I. Marks, et al., Induction of Immunity Against Lethal *Haemophilus influenzae* Type b Infection by *Escherichia coli* Core Lipopolysaccharide, J. Clin. Invest., vol. 69, Apr. 1982, pp. 742-749.
A. I. Braude, et al., Protection against Gram-Negative Bacteremia with Antiserum to Endotoxins, Antiserum to LPS of Gram-Negative Bacteria, pp. 111-125.

*Primary Examiner*—Howard E. Schain
*Attorney, Agent, or Firm*—Wegner & Bretschneider

[57] ABSTRACT

A composition for co-injection of an animal against a gram-negative pathogen which comprises an effective dose of a gram-negative type lipopolysaccharide devoid of O-carbohydrate side-chains and a bacterin derived from said pathogen. Methods of co-injection of an animal to protect the animal against gram-negative pathogens are also discussed.

17 Claims, No Drawings

CO-VACCINATION USING NON-O-CARBOHYDRATE SIDE-CHAIN GRAM-NEGATIVE BACTERIA PREPARATION

This application is a continuation-in-part of U.S. Ser. No. 866,451, filed May 23, 1986, now abandoned.

FIELD OF THE INVENTION

This invention relates to an improved composition for co-vaccination of animals, including mammals and birds, against gram-negative organisms and the diseases caused thereby. More particularly, the invention concerns a co-vaccine that employs a bacterial lipopolysaccharide (LPS) fraction devoid of O-carbohydrate side-chains, exemplified by *E. coli* J5 and mutants thereof, with a bacterin directed to one or more gram-negative organisms for the immunological protection of an animal against gram-negative organisms, and the diseases caused by these organisms.

BACKGROUND OF THE INVENTION

Gram-negative bacteria have similar LPS structures. Some mutant gram-negative bacterial strains lack the O-carbohydrate side-chains normally associated with gram-negative bacteria. These mutant organisms lack pili and outer antigens which are normally associated with the LPS membrane leaving LPS and other core antigens exposed.

*Escherichia coli* strain J5 is a well known example of a genetically stable gram-negative bacterial species having LPS and other core antigens exposed. Other gram-negative bacteria of different species, such as *Salmonella enteritidis*, ATCC No. 53000, described in European patent application No. 0158282, also lack the O-carbohydrate side-chains (also known as "K antigens"). The European patent application teaches a method of preparing non-O-carbohydrate side-chain gram-negative bacteria.

SUMMARY OF THE INVENTION

In accordance with the present invention, a co-vaccine suitable for administration against gram-negative organisms which contains an effective dose of a bacterial lipopolysaccharide devoid of O-carbohydrate side-chains, bacterins of one or more gram-negative organisms, and optionally a pharmaceutically acceptable carrier, is disclosed. Administration of the co-vaccine is achieved by the co-injection of the bacterial lipopolysaccharide devoid of O-carbohydrate side-chains and the bacterins.

Also disclosed is a composition and method of enhancing the immune response, and thus protecting an animal against diseases caused by gram-negative organisms by co-injecting the animal with an effective amount of bacterial lipopolysaccharide (LPS) devoid of O-carbohydrate side-chains in combination with bacterins of one or more gram-negative organisms.

DETAILED DESCRIPTION OF THE INVENTION

The present invention relates to the co-administration of an effective amount of a bacterial lipopolysaccharide devoid of O-carbohydrate side-chains in conjunction with a vaccine specifically directed to each gram-negative organism to which immunization is desired. It has been found that bacterial lipopolysaccharide devoid of O-carbohydrate side-chains is an effective immunomodulator when used in conjunction with gram-negative bacterins.

It has been found that the process of co-injection of bacterial LPS devoid of O-carbohydrate side-chains in combination with gram-negative bacteria provides an advantage over gram-negative bacterin preparations used alone. The process of co-injection encompasses contemporaneous administration.

The co-vaccine of the present invention may optionally be administered in admixture with a pharmacologically acceptable carrier prior to administration to an animal. Pharmacologically acceptable carriers for the invention are those usually employed in vaccines such as aqueous and oil based carriers and includes slow release antigen/adjuvant combinations. Exemplary of components in such carriers are saline, aluminum hydroxide gel, and carboxypolymethylene.

A source of bacterial lipopolysaccharide devoid of O-carbohydrate side-chains is required. *E. coli* strain J5, or mutants thereof, is exemplary of a gram-negative organism having exposed LPS and other core antigens. *E. coli* strain J5 whole cells are a preferred source of bacterial lipopolysaccharide devoid of O-carbohydrate side-chains.

*E. coli* strain J5, i.e., ATCC No. 39355, can be cultivated in suitable growth media such as brain heart infusion or tryptic soy broth. Either enriched or minimal nutrient media can be used and the culture may be grown in glass containers or fermentors. A preferred medium is Trypticase Soy Broth (Difco Laboratories, Detroit, MI). Frozen or lyophilized J5 cultures can be used to inoculate the media.

The size of an inoculum should not be less than 0.2 percent v/v of the total volume. Growth of the organism is monitored by utilization of sugars, change in pH units and a change in the absorbance of the culture.

Gram-negative bacterial cells devoid of O-carbohydrate side-chains and bacterins of the present invention may be live or inactivated, and may be used in any combination thereof. A preferred source of bacterial lipopolysaccharide devoid of O-carbohydrate side-chains and bacterins of the present invention is inactivated cells. It is also preferred to use inactivated vaccines.

Gram-negative bacterial cells devoid of o-carbohydrate side-chains can be inactivated by boiling or treatment with anti-bacterial agents such as formaldehyde (0.2 percent v/v), beta-propriolactone, or antibiotics. The preferred method to inactivate the cells is with formaldehyde. The cell culture can then be optionally concentrated and/or washed to remove media components. Washed and concentrated cells devoid of O-carbohydrate side-chains are preferred.

The cell culture is typically concentrated from 5-50 percent by volume. One method to concentrate cells is the hollow-fiber method (Amicon Corporation, Danvers, MA). This method utilizes a hollow-fiber containing cartridge which includes a matrix of fibers through which the sample is pumped.

The preferred mode employs *E. coli* J5 cells, washed and concentrated to $2-3 \times 10^{10}$ cfu/ml as determined optically. This corresponds to an approximate twenty-fold dilution of a J5 cell culture.

Bacterins of various types of gram-negative organisms are useful in the present invention. Specific examples of gram-negative bacterin strains are the following:

*Pasteurella multocida, P. hemolytica, Escherichia coli, Bordetella bronchiseptica, Salmonella typhimurium,*

S. choleraesuis, S. dublin, Pseudomonas aeruginosa, Haemophilus pleuropneumoniae, H. parasuis, H. sommnus, Moraxella bovis, Treponema hyodysenteriae, Campylobacter sputurum, C. hyointestinalis, Leptospira canicola, L. grippotyphosa, L. hardjo, L. icterohaemorrhagiae, L. pomoma, and L. bratislava. Bacterins useful in the present invention are prepared, grown and inactivated, according to the techniques known per se. Whole cell preparations are a preferred source of bacterins.

In the preparation of the compositions of the invention, the bacterins are preferably thoroughly mixed with the bacterial lipopolysaccharide devoid of O-carbohydrate sidechains. The admixture of the bacterin or bacterins with the bacterial lipopolysaccharide devoid of O-carbohydrate sidechains can occur during the formulation of the bacterin or after the bacterin itself has been prepared.

The bacterial lipopolysaccharide devoid of O-carbohydrates and bacterin is co-administered either undiluted or diluted with a pharmacological saline solution. Significant favorable results have been obtained with dilution values of up to about 1:25 with a number of pathogens tested. In numerous experiments undiluted or diluted solutions of about 1:5 have given very favorable results. Each milliliter of vaccine preparation preferably contains $6-600 \times 10^8$ cfu/ml of E. coli, or other source of bacterial lipopolysaccharide devoid of o-carbohydrates, and bactrins, respectively.

The co-vaccine composition can be used to enhance the immune response, and thus protect animals prior to infection of the animals with the gram-negative pathogen for which the inoculation is prepared. The co-vaccine can also be used to stimulate the immune response, and thus protect animals currently infected with the gram-negative pathogen for which the inoculation is prepared.

This invention can be used with animals having a antigen/antibody immune response system. Specific animals in which the invention can be used include such domestic mammals as cattle, sheep, goats, pigs, dogs, cats, and horses as well as poultry animals. An approximate typical dose is 0.5–1.5 ml for poultry, 1.0–3 ml for pigs and 2–4 ml for cattle.

The following Examples are used to illustrate the invention further but should not be deemed to limit it in scope.

EXAMPLE 1

Production of J5 Bacterin

E. coli J5 Bacterin is produced by inoculating media with actively growing seed (ATCC No. 39355). During the growth phase, the temperature is kept at 37° C.±2° C. and the pH is held constant at 7.0–7.3. The growth is monitored and maintained at a pH of 7.0–7.3 by the addition of 5N sodium hydroxide. Dextrose is added as a sterile 50% solution to obtain maximum growth. At the end of the growth period the bacterin is inactivated with formaldehyde. After inactivation, tests are run to keep the free formaldehyde level below 0.2%.

EXAMPLE 2

J5 and Pasteurella Multocida

An E. coli J5 culture is grown and inactivated with formaldehyde as in Example 1. It is then concentrated to approximately 5–10% of its original volume and washed with 3 volumes of physiological saline solution.

The inactivated, concentrated E. coli J5 Bacterin is then well combined with Midcon Labs' Pasteurella Multocida (PM) bacterin in the following proportions:

| | |
|---|---|
| 97.5 ml. PM Bacterin | (25% solution) |
| 2.5 ml. J5 | |
| 95.0 ml. PM Bacterin | (50% solution) |
| 5.0 ml. J5 | |

The vaccine preparations are administered subcutaneously or intramuscularly, undiluted or in a 1:5 dilution. The diluent is sterile phosphate buffered saline solution.

The results of comparative tests of the Midcon Labs' PM bacterin, E. coli J5 bacterin, and a combination of E. coli J5 bacterin with the PM bacterin appear in Table 1. USDA Pasteurella multocida (PM) Standard Reference Bacterin, IRP 248 and PM Challenge Culture, IRP 255 is used in the testing as per USDA test protocols.

TABLE 1

| DILUTION | USDA PM STANDARD | MIDCON PM STANDARD | MIDCON PM WITH 25% J5 | MIDCON PM WITH 50% J5 | 25% J5 ONLY | UNVACCINATED CONTROLS |
|---|---|---|---|---|---|---|
| A. UNDILUTED | #101+ 12/20* | #201 11/20 | #301 17/19 | #401 13/19 | #501 4/20 | #601 0/20 |
| B. 1:5 | #102 1/20 | #202 1/20 | #302 4/20 | #402 1/20 | #502 0/20 | #602 X |

*No. Survivors/No. Challenged
+Cage No.
X No Mice in This Group

EXAMPLE 3

J5 and Salmonella Choleraesuis

A vaccine is prepared with E. coli J5 bacterin and Midcon Labs' Salmonella choleraesuis Bacterin, as in the procedures of Example 2.

The comparative test results of the use of either bacterin alone and the co-vaccine preparation of E. coli J5 bacterin and Salmonella choleraesuis bacterin appear in Table 2. The challenge culture is Salmonella choleraesuis, USDA IRP 224.

TABLE 2[1]

| DILUTION | SALMONELLA CHOLERAESUIS BACTERIN | SALMONELLA CHOLERAESUIS W/25% J-5 | SALMONELLA CHOLERAESUIS W/50% J-5 | 25% J-5 ONLY | 50% J-5 ONLY | UNVACCINATED CONTROLS |
|---|---|---|---|---|---|---|
| UNDILUTED | #201+ | #301 | #401 | #501 | #601 | #701 |

TABLE 2[1]-continued

| DILUTION | SALMONELLA CHOLERAESUIS BACTERIN | SALMONELLA CHOLERAESUIS W/25% J-5 | SALMONELLA CHOLERAESUIS W/50% J-5 | 25% J-5 ONLY | 50% J-5 ONLY | UNVAC- CINATED CONTROLS |
|---|---|---|---|---|---|---|
| 1:5 | 11/20* #202 4/20 | 15/20 #302 10/20 | 12/20 #402 5/20 | 3/20 #502 1/20 | 4/20 #602 1/20 | 0/20 #702 X |

*No. Survivors/No. Challenged
+Cage No.
X No Mice in This Group
[1]No USDA standard bacterin available.

EXAMPLE 4

J5 and E. coli

A vaccine is prepared with E. coli J5 bacterin and E. coli Bacterin Sero Type 987p, as in the procedures of Example 2.

Table 3 shows the results of tests of the use of either bacterin alone and the co-vaccine preparation of E. coli J5 bacterin and E. coli bacterin. A further dilution of the vaccine is tested at 1:25 as well.

TABLE 3[1]

| DILUTION | E COLI BACTERIN | E COLI W/25% J-5 | E COLI W/50% J-5 | 25% J-5 ONLY | 50% J-5 ONLY | UNVACCINATED CONTROLS |
|---|---|---|---|---|---|---|
| UNDILUTED | #201+ 12/20* | #301 20/20 | #401 20/20 | #501 14/20 | #601 13/20 | #701 0/20 |
| 1:5 | #202 6/20 | #302 20/20 | #402 18/20 | #502 8/20 | #602 10/20 | #702 X |
| 1:25 | #203 2/20 | #303 8/20 | #403 5/20 | #503 2/20 | #603 3/20 | #703 X |

*No. Survivors/No. Challenged
+Cage No.
X No Mice in This Group
[1]No USDA standard available.

EXAMPLE 5

8 ml of Salmonella typhimurium Standard Reference Bacterin NVSL #81 IRP STB Serial 1 is mixed with 2 ml of saline, undiluted E. coli J5, E. coli J5 diluted 1:10, E. coli J5 diluted 1:100 and E. coli J5 diluted 1:1000. The admixture is the further diluted 1:5 and 1:25 with saline. 20 8 week old White Swiss Webster mice from SASCO, Omaha, NE are used for each dilution. The mice are vaccinated with 0.1 ml IP twice 2 weeks apart. 14 days after the second vaccination, the mice are challenged with 0.25 ml of a 10[4] dilution of S. typhimurium.

Table 4 shows the results of the experiment S. typhimurium bacterin alone or in combination with E. coli J5 at various dilutions.

TABLE 4

| Dilution of S. typhimurium/E. coli J5 Bacterin Tested | | |
|---|---|---|
| VACCINE | 1:5 | 1:25 |
| J-5 Undiluted | 2/20* | 4/20 |
| J-5 1:10 | 1/20 | 4/20 |
| J-5 1:100 | 3/17 | 6/20 |
| J-5 1:1000 | 2/20 | 9/20 |
| No J-5 | 2/18 | 6/14 |

*No. of Dead/No. Challenged

EXAMPLE 6

8 ml of Midcon Labs' Pasteurella multocida is mixed with 2 ml of phosphate buffered saline, undiluted E. coli J5, E. coli J5 diluted 1:10, E. coli J5 diluted 1:100. The admixture is then either administered or further diluted to 1:5 with phosphate buffered saline.

Twenty six-week-old White Swiss Webster mice from SASCO, Omaha, Nebr. are used for each dilution. The mice are vaccinated with 0.1 ml IP and are challenged 14 days after the vaccination with 0.20 ml of a 10[6] dilution of the challenge strain (USDA strain 169).

Table 5 shows the results of the experiment using bacterin alone or in combination with E. coli J5 at various dilutions.

TABLE 5

| Dilution of P. Multocida/E. coli J5 Bacterin Tested | | |
|---|---|---|
| VACCINE | UNDILUTED | 1:5 |
| J-5 Undiluted | 4/20* | 11/20 |
| J-5 1:10 | 8/20 | 17/20 |
| J-5 1:100 | 6/20 | 14/20 |
| No J-5 | 10/20 | 12/20 |

*No. of dead/No. challenged.

EXAMPLE 7

A vaccine is prepared with E. coli J5 bacterin and Midcon Labs' Moraxella bovis (MB) as in the procedures of Example 2.

Cattle were vaccinated twice with either bacterin alone or the co-vaccine preparation of E. coli J5 bacterin and Moraxella bovis bacterin. The time lapse between the first and second vaccinations was 21 days. 25 days after the second vaccination the cattle were challenged with Moraxella bovis. The challenged cattle were examined 7, 15, 19, 29 and 40 days after challenge for visible gross ocular lesions.

Table 6 shows the results of the challenge testing.

TABLE 6

| DAYS AFTER CHALLENGE | MIDCON MB STANDARD | MIDCON MB WITH 25% J5 | MIDCON MB WITH 50% J5 | UNVACCINATED CONTROLS |
|---|---|---|---|---|
| 7 | 114/121* | 111/111 | 89/90 | 73/87 |
| 15 | 113/121 | 111/111 | 89/90 | 64/87 |
| 19 | 111/121 | 109/109+ | 86/90 | 50/86 |
| 29 | 110/121 | 109/109 | 84/90 | 39/86 |
| 40 | 110/121 | 109/109 | 84/90 | 37/86 |

*No. of Symptom Free Animals/No. Challenged.
+Two calves lost to an electrical storm.
^One infected calf lost to an electrical storm.

What is claimed is:

1. A composition effective for co-injection of an animal to enhance the immune response to said animal against a gram-negative pathogen which comprises an effective immune response enhancing dose of
   (a) bacterial lipopolysaccharide devoid of O-carbohydrate side-chains; and
   (b) a whole cell bacterin derived from said pathogen.

2. A composition as in claim 1, wherein said lipopolysaccharide is contained in cells of gram-negative bacteria.

3. A composition as in claim 2, wherein said cells of gram-negative bacteria are E. coli J5 or mutants thereof.

4. A composition of claim 1, wherein said pathogen is one or more selected from the group consisting of Pasteurella multocida, P. hemolytica, Escherichia coli, Bordetella bronchiseptica, Salmonella typhimurium, S. choleraesuis, S. dublin, Pseudomonas aeruginosa, Haemophilus pleuropneumoniae, H. parasuis, H. sommnus, Moraxella bovis, Treponema hyodysenteriae, Campylobacter sputurum, C. hyointestinalis, Leptospira canicola, L. grippotyphosa, L. hardjo, L. icterohaemorrhagiae, L. pomoma, and L. bratislava.

5. A composition of claim 3, wherein said pathogen is one or more selected from the group consisting of Pasteurella multocida, P. hemolytica, Escherichia coli, Bordetella bronchiseptica, Salmonella typhimurium, S. choleraesuis, S. dublin, Pseudomonas aeruginosa, Haemophilus pleuropneumoniae, H. parasuis, H. sommnus, Moraxella bovis, Treponema hyodysenteriae, Campylobacter sputurum, C. hyointestinalis, Leptospira canicola, L. grippotyphosa, L. hardjo, L. icterohaemorrhagiae, L. pomoma, and L. bratislava.

6. A composition as in claim 2, wherein said gram-negative cells are concentrated to about 5 to about 50 percent by volume.

7. A composition as in claim 3, wherein said gram-negative cells are concentrated to about $2-3 \times 10^{10}$ cfu/ml.

8. Process of enhancing the immune response of an animal susceptible to infection by a gram-negative pathogen which comprises co-injection of an effective immune response enhancing dose of
   (a) bacterial lipopolysaccharide devoid of O-carbohydrate side-chains; and
   (b) a whole cell bacterin derived from said pathogen.

9. A process as in claim 8, wherein said lipopolysaccharide is contained in cells of gram-negative bacteria.

10. A process as in claim 9, wherein said gram-negative cells are E. coli J5 or mutants thereof.

11. A process of claim 8, wherein said pathogen is one or more selected from the group consisting of Pasteurella multocida, P. hemolytica, Escherichia coli, Bordetella bronchiseptica, Salmonella typhimurium, S. choleraesuis, S. dublin, Pseudomonas aeruginosa, Haemophilus pleuropneumoniae, H. parasuis, H. sommnus, Moraxella bovis, Treponema hyodysenteriae, Campylobacter sputurum, C. hyointestinalis, Leptospira canicola, L. grippotyphosa, L. hardjo, L. icterohaemorrhagiae, L. pomoma, and L. bratislava.

12. A process of claim 10, wherein said pathogen is one or more selected from the group consisting of Pasteurella multocida, P. hemolytica, Escherichia coli, Bordetella bronchiseptica, Salmonella typhimurium, S. choleraesuis, S. dublin, Pseudomonas aeruginosa, Haemophilus pleuropneumoniae, H. parasuis, H. sommnus, Moraxella bovis, Treponema hyodysenteriae, Campylobacter sputurum, C. hyointestinalis, Leptospira canicola, L. grippotyphosa, L. hardjo, L. icterohaemorrhagiae, L. pomoma, and L. bratislava.

13. A process as in claim 9, wherein said gram-negative cells are concentrated to about 5 to about 50 percent by volume.

14. A process as in claim 10, wherein said gram-negative cells are concentrated to about $2-3 \times 10^{10}$ cfu/ml.

15. A process of claim 10, wherein the animal is selected from the group consisting of cattle, pigs, horses, dogs, cats, sheep, goats and poultry animals.

16. A process as in claim 10, wherein the co-vaccine which also comprises a pharmacologically acceptable carrier.

17. A process as in claim 10, wherein said pharmacologically acceptable carrier is selected from the group consisting of aqueous or oil based carriers.

* * * * *